United States Patent [19]

Staar

[11] 4,275,840
[45] Jun. 30, 1981

[54] PACKAGE FOR STORING AND SPRAYING SMALL AMOUNTS OF LIQUIDS

[75] Inventor: Marcel J. H. Staar, Brussels, Belgium

[73] Assignee: Panpack A.G., Vaduz, Liechtenstein

[21] Appl. No.: 55,515

[22] Filed: Jul. 9, 1979

[30] Foreign Application Priority Data

Dec. 15, 1978 [BE] Belgium .................................. 872803
Jun. 5, 1979 [DE] Fed. Rep. of Germany ....... 2922740

[51] Int. Cl.³ ............................................. B65D 1/32
[52] U.S. Cl. ..................................... 239/327; 222/107; 222/215; 222/541; 239/399
[58] Field of Search ....................... 239/326, 327, 399; 222/107, 206, 215, 541

[56] References Cited

U.S. PATENT DOCUMENTS

| 2,707,581 | 5/1955 | Kaplan | 222/107 |
| 2,786,717 | 3/1957 | Rausch | 239/327 |
| 3,897,005 | 7/1975 | Reiner | 239/327 |

Primary Examiner—Richard A. Schacher
Attorney, Agent, or Firm—Leydig, Voit, Osann, Mayer & Holt, Ltd.

[57] ABSTRACT

The package for storing and spraying small amounts of liquid comprises a formed section and a flat sheet joined together such that together they provide a compressible container for storing liquid and a conterminous system of passageways for conveying and accelerating the liquid when pressure is applied to the container, said passageway system being constructed to keep the liquid within the container without any outside means of assistance. The passageway system terminates tangentially in a turbulence space provided with at least one central nozzle aperture. To intensify the spraying effect or atomization of the liquid, two passageways are provided between the container and the turbulence space which terminate tangentially in the turbulence space offset at an angle of 180°. The means designed to keep the liquid within the container consists preferably of a ruptureable seal at a site between the container and the passageway system.

18 Claims, 11 Drawing Figures

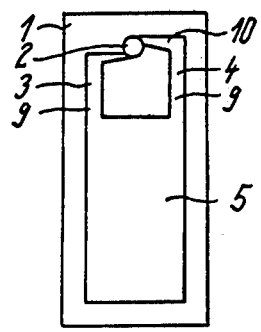 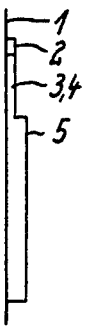 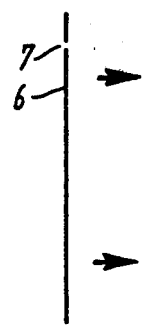 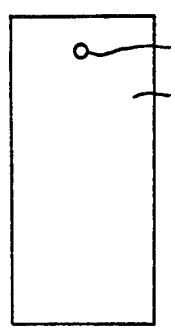
Fig.1　Fig.2　Fig.3　Fig.4
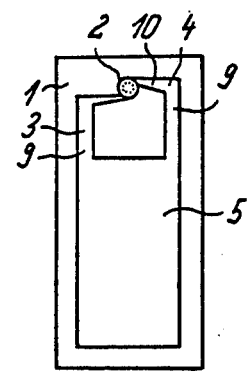 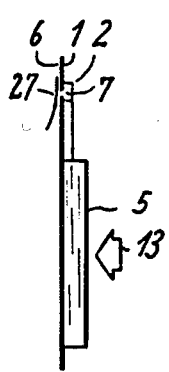 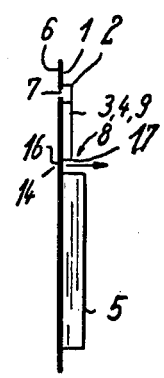 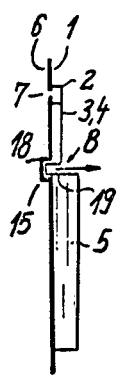
Fig.5　Fig.6　Fig.7　Fig.8
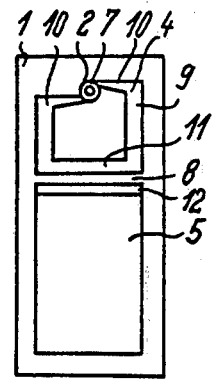 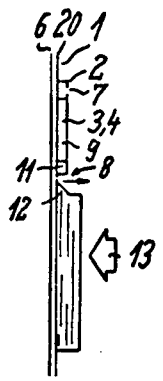 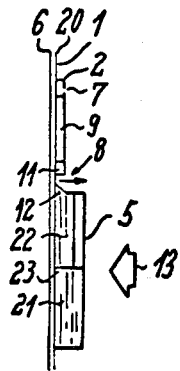
Fig.9　Fig.10　Fig.11

PACKAGE FOR STORING AND SPRAYING SMALL AMOUNTS OF LIQUIDS

DESCRIPTION OF THE INVENTION

This invention relates to a package for storing and spraying small amounts of liquid, said package being formed of two thin sheet portions which have a configuration when joined together to provide a compressible sealed container for storing the liquid, a conterminous system of passageways for conveying and a nozzle for spraying said liquid.

Small packages are already known which accommodate shampoo pastes and which have a neck formed at one corner thereof. A handle is located at the free end of the neck which permits the user to twist off the neck, thereby removing the handle and forming an irregular passageway aperture with burrs and jutting edges. Since in order to hold the small package the user must exert pressure on the container with the shampoo, he runs the risk of squeezing the shampoo out immediately upon opening the passageway. In order to avoid this to a certain extent, it is also known as disclosed in U.S. Pat. No. 3,897,005, to open a system of passageways by cutting off one corner of the package, thus permitting not only the liquid but also the air inside the package to be expelled at the same time, thereby achieving a spraying effect. This spraying effect, however, is only effected when the package is held in an upright position while expelling the liquid. In this position, the air and liquid will be ejected in equal amounts. Moreover, the spraying effect is dependent on the fact that the cut be made in a precisely predetermined manner, since the system of passageways would otherwise have one or more apertures which would interfere with obtaining the desired spraying effect. Both factors limit the usefulness and commodity value of the known packages considerably.

By contrast, the object of the present invention is to provide a package for storing and spraying small amounts of liquid which is adapted to be opened in a precisely predetermined manner without outside means of assistance, for instance by the application of pressure exclusively.

To accomplish this object with a package formed of two thin sheet portions which have a configuration when joined together to provide a compressible sealed container for storing liquid, a system of passageways and nozzle for spraying the liquid, the invention proposes that the passageway system be constructed to keep the liquid within the container and to accelerate said liquid when pressure is applied to the compressible container, said passageway system terminating tangentially in at least one turbulence space provided with at least one central nozzle aperture.

It is advantageous that the package of this invention can be opened without requiring scissors or other means of assistance. The liquid is stored in the container and, when the nozzle aperture is closed off (as by a removable adhesive tab), is retained by the air in the passageway system or is separated by a predetermined rupture site from said passageway system which opens externally. For instance, if the thumb applies a first pressure to the container, the predetermined rupture site will be opened and some liquid will enter the system of passageways, thereby expelling the air located therein through the nozzle which is always open. As more pressure continues to be applied to the container, this empties its contents into the passageway system, the passageway system having a cross section which diminishes in size in the direction of the nozzle aperture, thereby accelerating the liquid. A whirling motion or angular momentum is imparted to the already accelerated liquid in the turbulence space before it emerges from the nozzle aperture in a finely atomized state. An approximately conical mist of very fine fog-like droplets of liquid is formed in this way with the apex of the cone being located in the vortex within the circular space. In so doing, none of the liquid is lost and the conical spray always has a constant shape, since the system of passageways does not have to be opened by means of tools, but, together with the turbulence space and the nozzle aperture, is already open when manufactured and remains open even during transport and storage of the packages. The manufacture of the package is simplified, since the thin sheet including the container, the system of passageways and the turbulence space only needs to be stamped or deep-drawn. The container is thereafter filled and the shaped thin sheet is joined with a flat thin sheet. As a last step, the individual, filled packages can be cut off the train of packages. This can occur at the same time the thin sheets are joined together, preferably by fusing them together.

The package is designed for a single use and can accommodate many different types of liquids. It can be utilized in particular for perfume, toilet water, hair spray and the like. It can also be used as well to spray sterilized or sterilizing substances in the field of medicine. The closed package, if desired packed in another envelope, can be sterilized by ultraviolet radiation, for example, the outer envelope being removed in the operating theatre, the surgeon pressing on the container to open the predetermined rupture site and directly sterilizing the site to be treated. It is an advantage that the package contains no propellants and does not require any foreign bodies either to close or to open it. The spray package can also be used in the food and beverage sector, for example for oil or vinegar. The container can even be designed as a mixing container in which the first pressure applied removes or ruptures a partition, thus enabling the liquids located inside the container to mix with one another before they enter the system of passageways and are sprayed out of the package.

The liquid may also be a specific amount of paint which is sprayed onto damaged parts of motor vehicles, for instance, for the purpose of repairing them.

The package is also suitable for spraying other liquids such as insecticides and herbicides (weed killers).

In order to intensify the spraying or atomizing effect, it is also provided that two passageways be provided between the container and the turbulence space which are offset at an angle of 180° and terminate tangentially in said turbulence space.

If the compressible container, the passageways and the turbulence space are formed in a thermoplastic sheet, it is expedient to make the nozzle aperture at the same time the sheet is formed. This aperture is then located in the inherently stable wall of the turbulence space which is just as insensitive to impact as are the walls of the passageways, since the original thickness of the plastic sheet remains essentially the same.

Other advantageous developments and embodiments of the invention will be clear from the drawings.

The drawing illustrates embodiments of the invention which will now be explained in detail with reference to the following description of the figures, in which:

FIG. 1 shows a top elevation of a formed sheet which comprises one section of a complete package;

FIG. 2 shows a side elevation of the formed sheet section according to FIG. 1;

FIG. 3 shows a side elevation of a planar sheet which comprises the second section of a complete package;

FIG. 4 shows a top elevation of the planar sheet section according to FIG. 3;

FIG. 5 shows a top elevation of the formed sheet section joined to the planar sheet section to provide a complete package in accordance with the invention;

FIG. 6 shows a side elevation of the formed sheet section joined to the planar sheet section according to FIG. 5 to provide a complete package;

FIG. 7 shows a side elevation of the complete package after formation of a predetermined rupture site in the two joined sections in accordance with a first alternative embodiment of this invention;

FIG. 8 shows a side elevation of the complete package after formation of a predetermined rupture site in accordance with a second alternative embodiment;

FIG. 9 shows a top elevation of the complete package according to a third alternative embodiment;

FIG. 10 shows a side elevation of the package according to FIG. 9;

FIG. 11 shows a side elevation of the package in accordance with a fourth alternative embodiment.

Turning to the drawings, different embodiments of packages constructed according to the invention are shown in FIGS. 6, 7, 8, 10 and 11. Considering first the package of FIG. 6, it is made by assembling a formed section 1 and and a flat sheet 6 shown in FIGS. 2 and 3, respectively.

FIGS. 1 and 2 show the section 1 formed from a thin sheet of thermoplastic material which is preferably polyethylene, and which has been separated from a train or web of interconnected formed sections. The package section 1 is expediently translucent and is formed as by vacuum forming or stamping to provide a turbulence space 2 connected through two passageways 3 and 4 to a container 5 which is compressible and designed to receive a small quantity of liquid. The container 5 has a greater depth and volume than the turbulence space 2 and passageways 3 and 4 so that the liquid is accelerated within the passageways 3 and 4 when (in the complete package of FIG. 6) the container 5 is compressed to force the liquid stored therein through the passageways to the space 2. In this first embodiment of this invention, a planar sheet 6 has a nozzle aperture 7, and is of a material such as thermoplastic, aluminum foil, or other material capable of being bonded to the formed section 1 to provide the complete package. When joining the formed section 1 and the planar sheet 6 as indicated by the arrows between FIGS. 2 and 3, the nozzle aperture 7 is aligned accurately to the center of the substantially circular turbulence space 2. The two passageways 3 and 4 are provided between the container 5 and the turbulence space 2 and terminate tangentially in said turbulence space 2 offset at an angle of 180°. The terminating portions of both passageways preferably have a conical configuration and taper from the container 5 toward the turbulence space 2. The nozzle aperture 7 of the turbulence space 2 is closed by a removable adhesive tab 27 in accordance with FIG. 6. The air trapped inside the two passageways 3 and 4 keeps the liquid in the container 5. Passageways 3 and 4 have parallel passageway segments 9 of substantially constant cross section as well as approximately right-angled terminating portions 10 at the free ends thereof, said terminating portions being oriented tangentially relative to the turbulence space 2 at diametrically opposite positions.

In Accordance with a preferred form of the invention shown in FIG. 7, the tab 27 is replaced by a ruptureable seal provided as shown in FIGS. 9-11 adjacent the rupture site 8 which communicates with both passageways 3 and 4, but which remains separated from the container 5 by the ruptureable seal at the site 8 as long as the liquid is enclosed in the container 5. In order to more easily rupture or separate the ruptureable seal, the container 5 can be beveled adjacent the rupture site 8—as illustrated at 12—to exert a wedge action on the sealed area 8 when finger pressure is applied in the direction of the arrow 13 in FIG. 6.

In the embodiment in accordance with FIG. 7, the ruptureable seal at the site 8 is provided as an adhesive connection 14 by cementing or glueing a groove 17 stamped into the formed section 1 to a location 16 on the planar sheet 6. The adhesive connection must be such as to provide a light, separable connection between the formed section 1 and the flat sheet 6 in the area 8 entirely across the end of the container 5 as shown in FIG. 9, so that when pressure is applied to the container 5 the liquid will be forced to the area 8 and the connection will be separated to permit the liquid to enter the passages 3, 4 from the container 5.

In the embodiment in accordance with FIG. 8, the ruptureable seal at the site 8 is formed by deep-stamping it 15 upon joining or subsequent to joining the formed section 1 to the planar sheet 6, thereby producing in the planar sheet 6 a projecting bead 18 which sealingly engages a recessed bead 19 in the formed section 1.

In accordance with a preferred form of the invention, as shown in FIGS. 9 and 10, the planar sheet 6 is preferably aluminum foil coated with a thermoplastic film 20 such as polyethylene. Both the aluminum foil 6 and the polyethylene film 20 have no holes or perforations and the nozzle aperture 7 is made in the center of the turbulence space 2 at the same time the section 1 is formed. After the container 5 has been filled with liquid, the formed section 1 and the planar foil sheet coated with a thin polyethylene film 20, are bonded together by heat and pressure such that a container for the liquid is formed which is closed on all sides, whilst the entire system of passageways 11, 9, 10 remains open and communicates with the turbulence space 2. To provide the ruptureable seal at the site 8, either the bond between the section 7 and the film 20 is weak enough to separate or the bond of the film 20 to the aluminum foil 6 is weak at least in the area of the site 8 to rupture. Thus, when an initial pressure is applied to the container 5 as shown by arrow 13, a passageway is opened such that the liquid will be able to flow unimpededly into the passageways 3, 4 adjacent the beveled area 12 through the open rupture site 8, from the container 5.

In the embodiment in accordance with FIG. 11, the container 5 is designed as a dual-chamber container, one chamber 21 being filled completely with a liquid, whilst another chamber 22 contains air in addition to another liquid. Between the two chambers 21 and 22 there is located a partition 23 which ruptures when an initial pressure is applied to the chamber 21 as indicated by arrow 13. The liquids from both chambers 21 and 22 can be mixed in this way inside the container 5. The ruptureable seal at the site 8 is thereafter opened by further pressure, whereupon the mixture can be sprayed by expelling it from the nozzle aperture 7 by continuous application of additional pressure.

While it is preferred that the flat sheet 6 is aluminum foil with a coating or film of polyethylene, and the formed section 5 is also polyethylene, both the flat sheet 6 and section 1 can be of other thermoplastic material, for instance polyvinyl chloride (PVC), and can also be laminated with the thin polyethylene film 20. Alternately, the formed section 1 and the planar sheet 6 can be made integral, both expediently being joined together along one of the longer edges and adapted to be folded along that edge. After filling the container 5, the planar segment 6 can be folded over the formed section 1. Subsequently both segments are sealingly fused together.

I claim:

1. A package for storing and spraying small amounts of liquid, said package comprising two sheet sections which are joined, and together provide a compressible container for storing, a conterminous system of passageways for conveying and a nozzle for spraying said liquid, said passageway system receiving liquid from the container and accelerating said liquid when pressure is applied to said container, said passageway system terminating substantially tangentially in at least one substantially circular turbulence space for imparting a whirling motion to liquid conveyed to said space, said turbulence space having at least one central nozzle aperture for discharging the liquid from the turbulence space in the form of a spray.

2. A package according to claim 1, including means to keep the liquid within the container comprising a tab which closes off said nozzle aperture and which can be removed therefrom.

3. A package according to claim 1, including means to keep the liquid within the container comprising a ruptureable seal at a site between said passageway system and said container.

4. A package according to any one of claims 1-3, wherein said passageway system includes a plurality of passageways which terminate substantially tangentially in the turbulence space offset at equal circumferential angles.

5. A package according to any one of claims 1-3, wherein said passageway system includes two passageways provided between said container and said turbulence space which terminate substantially tangentially in said turbulence space offset at an angle of 180°.

6. A package according to any one of claims 1-3, wherein said passageway system includes a plurality of passageways which terminate substantially tangentially in said turbulence space and said sheet sections further provide an antechamber adjacent to said container, said antechamber being separated from said container by a ruptureable seal and communicating with said passageway system.

7. A package according to any one of claims 1-3, wherein said passageway system includes a plurality of passageways which terminate substantially tangentially in the turbulence space offset at equal circumferential angles and said passageways taper towards said turbulence space.

8. A package according to claim 1 wherein said passageway system includes parallel passageway segments extending from said container.

9. A package according to claim 8, wherein said parallel passageway segments have a substantially constant cross section and a tapering portion at the free ends thereof, said tapering portions terminating substantially tangentially in said turbulence space.

10. A package according to any one of claims 1-3, 8 or 9, wherein one of said sheet sections is a thermoplastic sheet formed to provide said compressible container, passageway system turbulence space, and the other sheet comprises a planar sheet bonded to said formed sheet.

11. A package according to any one of claims 1-3, 8 or 9, wherein one of said sheet sections is a thermoplastic sheet formed to provide said compressible container, passageway system and turbulence space, and the other sheet section comprises a planar sheet bonded to said formed sheet, and wherein said formed sheet section and planar sheet section have an integral design and are folded together along one edge.

12. A package according to any one of claims 1-3, 8 or 9, wherein one of said sheet sections is a thermoplastic sheet formed to provide said compressible container, passageway system, and turbulence space, and the other sheet section comprises a planar sheet including a thermoplastic film bonded to said formed sheet.

13. A package according to any one of claims 1-3, 8 or 9, wherein one of said sheet sections is a thermoplastic sheet formed to provide said compressible container, passageway system and turbulence space, and the other sheet section comprises a planar sheet including a metal foil coated with a thin thermoplastic film bonded to said formed sheet.

14. A package according to any one of claims 1-3, 8 or 9, wherein one of said sheet sections is a thermoplastic sheet formed to provide said compressible container, passageway system and turbulence space, and the other sheet section comprises a planar sheet including a thermoplastic film bonded to said formed sheet, and wherein said thermoplastic is polyethylene.

15. A package according to claim 1, wherein said sheet sections are joined to provide a ruptureable seal between said container and said passageway system, said seal being ruptureable to admit liquid from said container to said passageway system when pressure is applied to the container and liquid therein.

16. A package according to claim 15, wherein said container includes dual chambers.

17. A package according to claim 16, wherein one chamber of said container is completely filled with liquid and another chamber is only partially filled with another liquid, a partition being provided between said two chambers which ruptures more easily than said ruptureable seal when pressure is applied to the container for mixing both liquids within the container.

18. A package according to claim 1, wherein said sheet sections further provide an antechamber adjacent to said container, said antechamber being separated from said container by a ruptureable seal and communicating with said passageway system, and said passageway system includes a plurality of passageways which terminate substantially tangentially in the turbulence space offset at equal circumferential angles.

* * * * *